United States Patent [19]

Hellstrom et al.

[11] Patent Number: 4,906,562
[45] Date of Patent: Mar. 6, 1990

[54] MONOCOLONAL ANTIBODIES AND ANTIGEN FOR HUMAN NON-SMALL CELL LUNG CARCINOMAS

[75] Inventors: Ingegerd Hellstrom; Joseph P. Brown; Karl E. Hellstrom; Diane Horn; Peter Linsley, all of Seattle, Wash.

[73] Assignee: Oncogen, Seattle

[21] Appl. No.: 776,321

[22] Filed: Oct. 18, 1985

Related U.S. Application Data

[63] Continuation-in-part of Ser. No. 684,759, Dec. 21, 1984, abandoned.

[51] Int. Cl.$^4$ .................. G01N 33/53; G01N 33/542; G01N 33/546; G01N 33/574
[52] U.S. Cl. .................................. 435/7; 436/514; 436/536; 436/537; 436/547; 436/548; 435/240.27; 530/387; 530/828; 530/806
[58] Field of Search .............. 530/387, 389, 808, 828; 435/7, 240.26, 240.27; 436/548, 514, 536, 537, 542, 547

[56] References Cited

U.S. PATENT DOCUMENTS

| 4,507,391 | 3/1985 | Pukel et al. | 435/7 |
|---|---|---|---|
| 4,579,827 | 4/1986 | Sakamoto et al. | 435/7 |
| 4,675,287 | 6/1987 | Reisfeld et al. | 435/7 |
| 4,757,003 | 7/1988 | Matsumoto et al. | 435/7 |

OTHER PUBLICATIONS

U.S. Pat. No. 4,569,788, issued Feb. 11, 1986, filed May 18, 1983 entitled: "Monoclonal Antibodies Against Non-Small Cell Lung Cancers" by Mulshine et al.
Rosen et al., 1984, Caqncer Res., 44:2052–2061.
Varki et al., 1984, Cancer Res., 44:681–687.
Huang et al., 1983, Arch. Biochem. and Biophysics, 220(1):318–320.
Minna et al., 1981, In Vitro, 17(12): 1058–1070.
Cuttita et al., 1981, Proc. Nat'l. Acad. Sci., Sci., 78:4591–4595.
Sikora et al., 1981, Br. J. Cancer, 43:696–700.
U.S. Pat. No. 4,579,827, issued Apr. 1, 1986, filed Mar. 11, 1983 entitled: Monoclonal Antibodies to Human Gastrointestinal Cancers and Hybridoma Method of Produciton of the Monoclonal Antibodies, by Sakamoto et al.
U.S. Pat. No. 4,522,918 issued Jun. 11, 1985, filed Dec. 15, 1981, entitled Process for Producing Monoclonal Antibodies Reactive with Human Breast Cancer, by Schlom et al.
Colcher et al., 1981, Cancer Res., 41:1451–1459.
U.S. Pat. No. 4,507,391 issued Mar. 26, 1985, filed Apr. 12, 1982 entitled Method for Detecting the Presence of GD3 Ganglioside, by Pukel et al.
Kannagi et al., 1983, Cancer Res., 43:4997–5005.
Kniep et al., 1983, J. Immunol. 131:1591–1594.
Nudelman et al., 1982, J. Biol. Chem., 257:12752–12756.
Urdal et al., 1980, J. biol. Chem., 21:10509–10516.
Young et al., 1979, J. Exp. Med., 150:1008–1019.
Donald et al., 1984, Biochem. Soc. Trans., 12:596–599.
Blanchard et al., 1983, J. Biol. Chem., 258:7691–7695.
Iwamori et al., 1978, J. Biol. Chem., 248:740–742.
Svennerholm et al., 1973, J. Biol. Chem., 248:740–742.
Sears et al., 1984, Control. Oncol., 19:180–192.
Carrasquillo et al., 1984, Cancer Treatment Reports 68:317–328.
Larson et al., 1983, J. Clin. Invest., 72:2101–2114.
Larson et al., 1983, J. Nucl. Med., 24:123–129.
Garrigues et al., 1982, Int'l. J. Cancer. 29:511–515.
Yeh et al., 1982, Int. J. Cancer, 29:269–275.
Brown et al., 1981, Proc. Nat'l Acad. Sci., 78:539–543.
Brown et al., 1979, J. Immunol. Meth., 31:201–209.
Sternberger et al., 1979, Immunocytochemistry (John Wiley & Sons, New York), pp. 104–109.
Nepom et al., 1984, Proc. Nat'l. Acad. Sci., 81:2864–2867.
Ey et al., 1978, Immunochemistry, 15:429–436.
Kohler et al., 1975, Nature, 265:495–497.1.

Primary Examiner—Margaret Moskowitz
Assistant Examiner—Jeff Kushan
Attorney, Agent, or Firm—Pennie & Edmonds

[57] ABSTRACT

The present invention is concerned with novel monoclonal antibodies which define a glycolipid antigen associated with human non-small cell lung carcinomas ("NSCLC") and certain other human carcinomas. The antibodies bind to normal human cells to a much lesser degree than to tumor cells. The antibodies find use in diagnostic methods such as the detection of malignant cells associated with NSCLC and in therapeutic methods. Also disclosed in a novel glycolipid antigen. The invention also comprises a method for determining the presence of a malignant condition in lung tissue and other human tissue. The method involves examining the human tissue for the presence of a glycolipid antigen having the terminal carbohydrate sequence: GalNAc$\beta$1→4Gal$\beta$1→3GalNAc$\beta$1→4Gal$\beta$1→R.

28 Claims, No Drawings

MONOCOLONAL ANTIBODIES AND ANTIGEN FOR HUMAN NON-SMALL CELL LUNG CARCINOMAS

This application is a continuation-in-part of co-pending application U.S. Pat. Ser. No. 684,759, filed Dec. 21, 1984.

BACKGROUND OF THE INVENTION

1. Field of the Invention

Human lung carcinomas are responsible for most deaths from cancer among men and are in the process of overtaking breast carcinomas as the most frequent cause of cancer death among women (Cancer Facts and Figures, 1983). This disease can be divided into 4 major histological types, i.e., epidermoid (30%), adenocarcinoma (35%), large-cell undifferentiated (15%), and small-cell (20%). Most cases of lung carcinomas are incurable by chemotherapy and radiation therapy. Small cell lung carcinomas may respond to chemotherapy and radiation therapy by a reduction in size, but not a total cure. Complete surgical removal of the tumor appears to be the only effective therapy. Unfortunately, however, fewer than 30% of lung cancer patients have tumors which can be totally resected at diagnosis and of these, fewer than one-third survive 5 years after apparent complete surgical removal of all tumor. There is a great need, therefore, for methods that would make possible an earlier diagnosis of lung cancer, a better definition of the degree of cancer spread, and a more effective therapy.

Monoclonal antibodies may be used for all these purposes. A prerequisite, however, is to find antibodies to antigens that are more strongly expressed in lung cancer than in normal adult tissues. In view of the known heterogeneity of tumor cell populations, the presence of several determinants on the same antigen molecule, the anticipated differences between antigens with respect to their suitability as diagnostic markers as compared to therapeutic targets, and the different biological characteristics of different antibodies to the same antigen, a number of different antibodies may be needed.

2. Description of the Prior Art

Human monoclonal antibodies to lung cancer antigens are described by Sikora et al., *Br. J. Cancer* (1981) 43:696–700. Monoclonal antibodies that demonstrate specificity for several types of human lung cancer are disclosed by Cuttitta et al., *Proc. Natl. Acad. Sci. U.S.A.* (1981) 78:4591–4595. Antigens associated with a human lung adenocarcinoma defined by monoclonal antibodies are described by Varki et al., *Cancer Research* (1984) 44:681–687.

Mouse monoclonal antibodies to glycolipid ganglio-N-triosylceramide (alialo GM$_2$) are described by Young, et al., *J. Exp. Med.* (1979) 150:1008. Expression of asialo GM$_2$ on cells from patients with Hodgkin's disease is described by Kniep, et al., *J. Immunol.* (1983) 131:1591–1594.

U.S. patent application Ser. No. 667,521, filed Nov. 2, 1984, discloses certain monoclonal antibodies for human non-small cell lung carcinoma.

Continuous cultures of fused cells secreting antibody of predefined specificity are described by Köhler et al., *Nature* (1975) 265:495–497.

SUMMARY OF THE INVENTION

The present invention is concerned with novel monoclonal antibodies which define a determinant site on a glycolipid antigen associated with human non-small cell lung carcinoma (NSCLC) cells. The term "NSCLC cells" includes epidermoid carcinoma cells, adenocarcinoma cells, and large cell undifferentiated carcinoma cells. The determinant site may also be found on antigens of some other carcinomas, e.g., some carcinomas of the breast, and, thus, the antibodies of the invention will also bind to these other carcinoma cells. The present monoclonal antibodies bind to a much lesser degree to normal adult cells than to tumor cells. The term "bind to a much lesser degree" means that the binding will not be detectable by immunohistological techniques. The monoclonal antibodies are secreted by murine hybridomas.

The present invention also includes methods for determining the presence of a malignant condition in human lung tissue and other human tissue. The method involves examining the tissue for the presence of a glycolipid antigen having the terminal carbohydrate sequence:

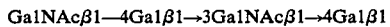

and related antigens such as a ganglio-N-triosylceramide, e.g., asialo GM$_2$. For example, the tissue can be contacted with an antibody which defines a determinant site on a cell associated glycolipid antigen having the above terminal carbohydrate sequence or a functional equivalent or fragment of such antibody.

Thus, the invention concerns certain diagnostic methods employing the monoclonal antibodies of the invention. One such method involves the determination of the presence of NSCLC cells in a specimen suspected of containing such cells. The specimen is contacted with the monoclonal antibody, which is capable of distinguishing such cells from other cell types which may be present in the specimen. The contact is carried out under conditions for binding of the antibody to such cells. After contact, the presence or absence of binding of the antibody to the cells in the specimen is determined. This binding is related to the presence or absence of the NSCLC cells in the specimen. Generally, the specimen is contacted with a labeled specific binding partner for the monoclonal antibody. This label is capable of producing a detectable signal. Another diagnostic method involves the localization to a tumor of antibodies or antibody fragments which have been properly labelled (e.g. with a radioisotope) and are subsequently injected into patients. This method can provide better ways to stage cancer patients with respect to extent of disease and to monitor changes in response to therapy.

The invention also has therapeutic applications. The antibodies can react with the above-mentioned antigen that is expressed in high concentrations at the tumor cell surface. It can mediate antibody-dependent cellular cytotoxicity (ADCC), that is, it can kill NSCLC cells (and certain other human carcinoma cells) in the presence of human lymphocytes or macrophages; it can activate human compliment so as to, for example, kill NSCLC cells in the presence of human serum. It can also be used as a carrier of various agents which have an anti-tumor effect, including, but not restricted to, chemotherapeutic drugs and radioisotopes.

DESCRIPTION OF THE SPECIFIC EMBODIMENTS

The present invention concerns novel antibodies which bind to an antigen on human NSCLC cells and certain diagnostic and therapeutic methods employing these antibodies. The monoclonal antibodies of the invention may be produced according to the standard techniques of Köhler and Milstein, supra. For example, human lung carcinoma cells from pleural effusions or cultured cells from human non-small cell lung carcinoma, or cells from a normal fetal lung, are used as the immunogen. These cells are injected into a mouse and, after a sufficient time, the mouse is sacrificed and spleen cells obtained. The spleen cell chromosomes encoding desired immunoglobulins are immortalized by fusing the spleen cells with myeloma cells or with lymphoma cells, generally in the presence of polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into the peritoneal cavity of a mammalian host, which accepts the cells, and harvesting the ascites fluid. Where an insufficient amount of the monoclonal antibody collects in the ascites fluid, the antibody is harvested from the blood of the host. Various conventional ways exist for isolation and purification of the monoclonal antibodies, so as to free the monoclonal antibodies from other proteins and other contaminants (see Köhler and Milstein, supra).

One monoclonal antibody in accordance with the present invention is designated L6. It defines a cell surface glycolipid antigen which we have identified as characteristic of human NSCLC cells and cells from certain other human carcinomas. On the basis of cross reactions of several known glycolipids with L6 antibody and the reactivity of asialo GalNAc—GM$_1$ with L6 antibody, we have concluded that the L6 glycolipid antigen has the following terminal sequence: GalNAcβ1→4Galβ1→3GalNAcβ1→4Galβ1→R wherein R is a carbohydrate that is as yet undefined. A particularly novel feature of the above antigen is that it is free of sialic acid residues and heretofore has not been known to be associated with human tissue. Sialosyl derivatives of the above terminal sequence have been described by Svennerholm et al., (1973) *J. Biol. Chem.* 248:740–742 and by Iwamori et al. (1978) *J. Biochem.* 84:1601. Furthermore, sialic acid derivatives of the above sequence have also been recognized as blood group Sd antigens by Donald et al. (1984) *Biochem. Soc. Trans.* 12: 596–599 and by Blanchard et al. (1983) *J. Biol. Chem.* 258:7691–7695. Therefore, one aspect of the present invention is a glycolipid antigen in purified form having the terminal carbohydrate sequence:

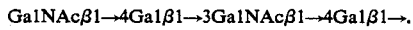

GalNAcβ1→4Galβ1→3GalNAcβ1→4Galβ1→.

The L6 antibody also precipitates a protein antigen from biosynthetically labelled NSCLC cells. This antigen is characterized by a band on sodium dodecylsulfate polyacrylamide gel electrophoreses (SDS - PAGE) with a molecular weight of about 20,000 daltons. This antibody is of the IgG2a isotype. It does not bind detectably to normal cells, such as fibroblasts, endothelial cells, or epithelial cells in the major organs. The L6 antibody is produced by the L6 murine hybridoma.

Also included within the scope of the invention are useful binding fragments of the above monoclonal antibody such as Fab, F(ab')$_2$, Fv fragments and so forth. The antibody fragments are obtained by conventional techniques. For example, useful binding fragments may be prepared by peptidase digestion of the antibody using papain or pepsin.

While the above specific example of the novel antibody of the invention is directed to an antibody binding to specific determinant sites on the respective antigens and being of the IgG2 sub-class from a murine source, this is not meant to be a limitation. The above antibody and those antibodies having functional equivalency with the above antibody, whether from a murine source, other mammalian source including human, or other sources, or combinations thereof are included within the scope of this invention, as well as other isotypes. By the term "functional equivalency" is meant that the antibody is capable of binding to the above-described determinant site and capable of competing with a particular antibody of the invention for such site. That is, such antibody, when combined with a specimen containing a cell or cell fragment having such determinant site, will bind to such determinant site and will block an antibody of the invention from binding to such site. Furthermore, since the antigen of the invention can have more than one determinant site, the invention includes monoclonal antibodies which define determinant sites other than determinant sites defined by the aforementioned monoclonal antibody.

The invention also includes the diagnostic and therapeutic use of the L6 antigen in humans and related antigens such as asialo GalNAc—GM$_1$ and asialo GM$_2$. The antigen can be purified by conventional methods such as immunoprecipitation as described by Yound et al., *J. Exp. Med.* (1979) 150:1008–1019.

One method of the invention involves the determination of the presence of a malignant condition in lung tissue and other human tissue by examining the tissue for the presence of a glycolipid antigen having the characteristics of the L6 antigen or of a ganglio-N-triosylceramide. The term "malignant condition" refers to the presence of dysplastic including carcinoma in situ, neoplastic, malignant, or tumor cells, or the like. The term "having the characteristics of" means that the antigen is reactive with an antibody which recognizes the L6 antigen or a related antigen such as asialo GalNAc—GM$_2$ or asialo—GM$_2$. For example, the specimen can be contacted or combined with a monoclonal antibody of the invention such as L6 antibody or an antibody having similar characteristics such as those described by Young, et al., supra, or Kniep, et al, supra. The contact is carried out under conditions for binding of the antibody to the malignant cells. After contact, the presence of binding of the antibody to the malignant cells in the specimen is observed. That is, the specimen is examined for immune complexes of the antibody and the antigenic site. This immune complex formation is related to the presence of malignant cells in the specimen. The invention also includes immune complexes of the L6 antibody or the L6 antigen.

A particular example, by way of illustration and not limitation, of a method in accordance with the invention is a method for the detection of tumor cells in excised tissue. The above method is applied to a specimen which is a section of the tumor obtained after removal of the tumor. The tumor that is excised is treated to obtain sections, which treatment initially involves freezing the tumor or tissue, normally freezing immediately after excision. The frozen layer of tissue is then cut into sections using, for example, a cryostat.

The section of the tumor obtained as described above is contacted with a monoclonal antibody of the invention and then with a second antibody directed against the above monoclonal antibody, which second antibody is labeled with a detectable label.

The excised specimen, e.g., the section of the tumor, is contacted with the first monoclonal antibody under conditions for binding of the antibody to the malignant cells. The incubation is generally conducted in an aqueous medium such as, for example, phosphate buffered saline containing a small amount of sodium azide, in a suitable container such as, for example, a glass petri dish, for a period from about 15 to 30 minutes at a temperature of from about 20° to 30° C. The amount of antibody employed is usually sufficient to provide detectable binding, i.e., to provide a detectable number of immune complexes between the antibody and the determinant or antigenic site in question.

Following the incubation, the section is washed to reduce or eliminate non-specifically bound antibody and then is examined to observe the above-mentioned complexes which result from binding of the monoclonal antibody to the cells of the specimen possessing the antigenic site. The binding is related to the presence of malignant cells in the section. Accordingly, binding is determined, for example, by contacting the specimen with a labeled specific binding partner for the monoclonal antibody. The label is capable of producing a detectable signal and may be a radioactive label, a chromophore such as a fluorescer, an enzyme, or the like.

An example of a technique employing the above approach is immunofluorescence staining. In this technique frozen sections of the tumor are fixed on a glass slide with acetone and are incubated with the monoclonal antibody in, for example, a petri dish. After washing with an appropriate buffer such as, for example, phosphate-buffered saline, the section is placed on a petri dish and contacted with the labeled specific binding partner for the monoclonal antibody, which may be, for example, a labeled antibody specific for the monoclonal antibody employed. Since, for the most part, the monoclonal antibody will be derived from a murine source, a labeled anti-mouse immunoglobulin specific for the monoclonal antibody may be employed. Such immunoglobulins may be raised according to standard techniques by injecting a suitable host with murine antibody, waiting for an appropriate time, and harvesting the anti-mouse immunoglobulins from the blood of the injected host.

After a second washing of the slide with, for example, an aqueous buffer, the sections may be covered with a fluorescent antibody mounting fluid and a coverslip and then examined with a fluorescence microscope to determine the binding of the monoclonal antibody to the section. The determination of the binding also may include an identification of the location of such binding within the specimen.

The binding of the monoclonal antibody to the specimen may also be determined by employing a monoclonal antibody which is covalently conjugated to a label capable of producing a detectable signal, such as a radioactive entity, a chromophore including dyes and fluorescers, or an enzyme. The number of labels employed per antibody is generally determined by the requirements of the diagnostic method in which the labeled antibody is employed and the availability of sites for linking the label to the antibody.

Methods for conjugating labels to antibodies and antibody fragments are well-known in the art. Such methods may be found in U.S. Pat. Nos. 4,220,450; 4,235,869; 3,935,074; and 3,996,345.

Another example of a technique in which the monoclonal antibody of the invention may be employed is immunoperoxidase labeling (Sternberger, *Immunocytochemistry*, John Wiley & Sons, N.Y., 1979, pp:104–169 as modified by Garrigues et al., *Int. J. Cancer* (1982) 29:511–515). The tissue to be tested is fixed with a suitable solvent, such as acetone, on a support, such as a glass slide. Next, the tissue is incubated with the monoclonal antibody and then washed free of unbound antibody. Then, the tissue is incubated with rabbit anti-mouse IgG, washed to remove unbound antibody, combined with mouse peroxidase-anti-peroxidase complex, washed to remove unbound conjugate, and then treated with substrate for the enzyme. Following this treatment the slide is examined for a detectable signal.

The antibodies of the invention may be used in a method of determining the presence of a malignant condition, for instance in an exfoliative cell specimen from the lung, such as sputum or in a cervical smear. By the term "exfoliative" is meant that the specimen comprises isolated cells or clumps of cells obtained by scraping or washing the surface of tissue, which cells are removed individually or in scales or laminae. The exfoliative cell specimen is to be distinguished from excised tissue such as that obtained by biopsy. Contact between the specimen and the antibody is made under conditions for binding of the antibody to the antigenic site. After contact, the presence or absence of binding of the antibody to the antigenic site is determined and is related to the presence of a malignant condition in the lung.

To determine the presence of a malignancy in the lung, a sputum sample would provide the exfoliative cell specimen to be used in the method. The method may find utility in the detection of a malignant condition in exfoliative cell specimens from the bronchus, gastro-intestinal tract including oral pharynx, mouth, etc.

The exfoliative cell specimen is next contacted with the aforementioned antibody under conditions for binding of the antibody to the specific antigenic site in the specimen to form antigen-antibody complexes. This antigenic site may be present on cells or cell fragments in the specimen. Generally, the specimen is placed on an appropriate support, such as, for example, a slide, usually glass, or some other suitable material. The exfoliative cell specimen is generally smeared on the slide to provide a thin layer of the specimen on the surface of the slide. The contact between the antibody and the specimen is generally carried out in an aqueous buffered medium. The buffers which may be employed include phosphate, tris, bicarbonate, etc. The pH is related to the nature of the specimen and the antibody, and is generally in the range of from about 5 to 8. The aqueous medium may additionally contain organic polar solvents in an amount of from about 0 to 40%. The organic polar solvents are water soluble and generally have from about 1 to 10 carbon atoms and from about 1 to 4 oxygen atoms. The antibody will be present in the aqueous medium at a concentration of about 1 to 100 µg/ml, preferably from about 10 to 20 µg/ml. The temperature during the contact of the specimen with the antibody is usually from about 4° to 40° C., preferably about 10° to 30° C. The period of contact is usually from about 15 to 120 minutes, preferably from about 30 to 60 minutes.

After the period of contact between the specimen and the antibody, the support is generally treated to remove unreacted antibody. Normally, this is accomplished by washing the support with an aqueous, usually buffered, medium. In general, the amount of wash solution should be sufficient to remove the unreacted antibody.

Next, the presence of antibody bound to the antigenic site in the specimen, which binding is related to the presence of a malignant condition at the locus, is observed. That is, the specimen is examined to determine the number of antigen-antibody (immune) complexes formed. It should be noted that in some instances very small numbers of the antigenic site in question may be found in the exfoliative cell specimen. However, in a malignant condition, large numbers of the antigenic site will be present and this latter condition is readily distinguishable by this method over a non-malignant condition because a large number of antigen-antibody complexes will be measurable where a malignant condition exists. To make the determination of the presence of binding, means for producing a detectable signal is incorporated into the assay system. For example, one may conjugate the antibody employed in the assay to a label which is capable of producing a detectable signal. The label may be a radioactive entity, a chromophore including dyes and fluorescers, an enzyme, or the like. The number of labels employed for the antibody is generally determined by the requirements of the method and the availability of sites for linking the label to the antibody.

Alternatively, one may contact the washed slide with a labeled specific binding partner for the antibody, which may be, for example, a labeled antibody specific for the antibody employed. Where the monoclonal antibody is derived from a murine source, a labeled anti-mouse immunoglobulin specific for the antibody employed in the method may be used. Such immunoglobulins may be raised according to standard techniques by injecting a suitable host with the monoclonal antibody, waiting for an appropriate time, and harvesting the anti-mouse immunoglobulins from the blood of the injected host. When a labeled specific binding partner for the antibody is employed, the slide must be washed again with an aqueous medium prior to examining the slide for fluorescence. The invention also includes anti-idiotypic antibodies prepared in response to the L6 antibody; such antibodies can be prepared with characteristics similar to those of the relevant tumor antigens (Nepom et al, (1984) *Proc. Natl. Acad. Sci.* 81:2864).

To determine the presence of binding between the antibody and the cell specimen where a fluorescer label is used, one may examine the slide for fluorescence, usually employing a fluorescence microscope. Where a label other than a fluorescer is employed, one may examine the slide or the specimen for the formation of a precipitate, a color, or the like.

The above description is directed primarily to the use of the antibodies of the invention in immunofluorescence techniques. However, the antibodies of the invention can be used in most assays involving antigen-antibody reactions. The assays may be homogeneous or heterogeneous. In a homogeneous assay approach, the specimen may be biological fluid such as serum, urine, and the like or the specimen may be lysed and clarified to remove debris. The immunological reaction usually involves the specific antibody, a labeled analyte, and the sample of interest. The signal arising from the label is modified, directly or indirectly, upon the binding of the antibody to the labeled analyte. Both the immunological reaction and detection of the extent thereof are carried out in a homogeneous solution. Immunochemical labels which may be employed include free radicals, fluorescent dyes, enzymes, bacteriophages, coenzymes, and so forth.

In a heterogeneous assay approach, the reagents are usually the specimen, the specific antibody, and means for producing a detectable signal. The specimen is generally placed on a support, such as a plate or a slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal includes the use of radioactive labels, fluorescers, enzymes, and so forth. Examplary of heterogeneous immunoassays are the radioimmunoassay, immunofluorescence methods, enzyme-linked immunoassays, and the like.

For a more detailed discussion of the above immunoassay techniques, see "Enzyme-Immunoassay," by Edward T. Maggio, CRC Press, Inc., Boca Raton, Fl., 1980. See also, for example, U.S. Pat. Nos. 3,690,834; 3,791,932; 3,817,837; 3,850,578; 3,853,987; 3,867,517; 3,901,654; 3,935,074; 3,984,533; 3,996,345; and 4,098,876, which listing is not intended to be exhaustive.

The antibodies of the invention can also be employed to image metastic deposits in human patients with NSCLC in a manner analogous to that described for malignant melanoma in *J. Nucl. Med.* (1983) 24:123–129 and in *J. Clin. Invest.* (1983) 72:2101–2114. The antibody or fragments thereof are radiolabelled and administered intravenously to a patient who subsequently is imaged using, e.g., a gamma camera or the like. Studies performed in thymusless, "nude" mice xenotransplanted with a human lung carcinoma have shown that $^{131}$I-labelled Fab fragments prepared from L6 localize selectively in the transplanted tumor. This indicates, on the basis of previous studies on melanomas (*J. Nucl. Med.* (1983) 24:123–129; *J. Clin. Invest.* (1983) 72:2101–2114) that tumor selective localization of L6, and antibody fragments prepared from L6, is likely following injection of human patients.

The invention also includes diagnostic kits for carrying out the methods disclosed above. In one embodiment, the diagnostic kit comprises (a) a monoclonal antibody more specifically defined above and (b) a conjugate of a specific binding partner for the above monoclonal antibody and a label capable of producing a detectable signal. The reagents may also include ancillary agents such as buffering agents and protein stabilizing agents, e.g., polysaccharides and the like. The diagnostic kit may further include, where necessary, other members of the signal-producing system of which system the label is a member, agents for reducing background interference in a test, control reagents, apparatus for conducting a test, and the like. In another embodiment, the diagnostic kit comprises a conjugate of a monoclonal antibody of the invention and a label capable of producing a detectable signal. Ancillary agents as mentioned above may also be present.

The antibodies of the invention may be used therapeutically. Antibodies with the proper biological properties are useful directly as therapeutic agents. Antibody L6 has such a property, since it can, when combined with human lymphocytes or macrophages, mediate antibody dependent cellular cytotoxicity (ADCC) in vitro. That is, it can cause the destruction of human NSCLC cells, as can be detected, for example, by using a technique in which the cancer cells are labelled with $^{51}Cr$ and incubated with the lymphocytes and antibody. Analogous studies have been performed with anti-melanoma antibodies and have shown that antibodies with high ADCC can inhibit outgrowth of human melanoma in nude mice. Since the L6 antibody is of the IgG2a isotype, it may also be able to activate macrophages (Sears, et al, *Contrl. Oncol. Karger, Basel*, (1984) 19:180–192). Furthermore, the antibody can be bound to a toxin to form an immunotoxin or to a radioactive material or drug to form a radiopharmaceutical or pharmaceutical. Methods for producing immunotoxins and radiopharmaceuticals of antibodies are well-known (see, for example, *Cancer Treatment Reports* (1984) 68:317–328). Furthermore, the L6 antibody can activate human complement so as to, for example, kill NSCLC cells in the presence of human serum.

Therefore, the invention includes a method for reducing or eliminating the population of non-small cell lung carcinoma cells in a host, which comprises administering to the host an amount of L6 antibody or a derivative thereof sufficient to cause a reduction in or elimination of the population of non-small cell lung carcinoma cells. By a derivative of the L6 antibody is meant that the L6 antibody is bound to a substance which assists in reducing or eliminating such population of cells, e.g., a toxin or a radioactive substance.

Another therapeutic use of the monoclonal antibody of the present invention is the immunization of a patient with an anti-idiotypic antibody raised by using one of the present monoclonal antibodies as an immunogen. Such immunization can induce an active anti-tumor activity (see, for example, Nepom et al.; *Proc. Natl. Acad. Sci. U.S.A.* (1984) 81:2864–2867. In a similar approach, the patient can be immunized with the L6 antigen in purified form, or a modified form of the antigen.

An attractive aspect of the present invention is that the present antibodies can be combined with other antibodies to NSCLC such as those disclosed in U.S. patent application Ser. No. 667,521, filed Nov. 2, 1984. The combination is effective in detecting at least the types of lung carcinomas mentioned above, namely, large cell undifferentiated lung carcinoma, adenocarcinoma, and epidermoid carcinoma.

The monoclonal antibodies of the invention also define determinant sites on antigens associated with other carcinomas such as breast carcinomas. Consequently, the present antibodies can find use in diagnostic and therapeutic products directed to such carcinomas.

EXAMPLES

The invention is further demonstrated by the following illustrative Examples. A number of procedures employed will be described first.

Immunohistological Technique

For immunohistological studies on frozen sections, the unlabelled antibody technique of Sternberger in *Immunochemistry*, John Wiley & Sons, N. Y. 1979, pp:104–169, as modified by Garrigues et al. in *Int. J. Cancer* (1982) 29:511–515, was used. The target tissues for these tests were obtained at surgery and frozen within 4 hr of removal in isopentane which had been precooled in liquid nitrogen. Tissues were then stored in liquid nitrogen or at −70° C. until use. Rabbit anti-mouse IgG (Sternberger-Meyer Immunochemicals, Inc., Jarettsville, Md.) was used at a dilution of 1/50. Mouse peroxidase-antiperoxidase complex (PAP, Sternberger-Meyer Immunochemicals, Inc.) containing 2 mg/ml of specifically purified PAP was used at a dilution of 1/80. Frozen sections were prepared, dried, treated with acetone and dried (Garrigues et al., 1982). Sections to be used for histologic evaluation were stained with hematoxylin. To decrease nonspecific background, sections were preincubated with normal human serum diluted 1/5 (Garrigues et al., 1982). Mouse antibodies, goat anti-mouse IgG, and mouse PAP were diluted in a solution of 10% normal human serum and 3% rabbit serum.

The staining procedure consisted of treating serial sections with either specific or control antibody for 2.5 hr, incubating for 30 min with rabbit anti-mouse IgG diluted 1/50, and exposing for 30 min to mouse PAP complex diluted 1/80. After each treatment with antibody, the slides were washed twice in phosphate buffered saline (PBS). The immunohistochemical reaction was developed with freshly prepared 0.05% 3,3'-diaminobenzidine tetrahydrochloride (Sigma, St. Louis, Mo.) and 0.01% hydrogen peroxide in 0.05M Tris buffer, pH 7.6 for 8 min. Further exposure to a 1% $OsO_4$ solution in distilled water for 20 min intensified the stain. The sections were rinsed with water, dehydrated in alcohol, cleared in xylene, and mounted on slides.

The slides were each read under code and coded samples were checked by an independent investigator. Typical slides were photographed by using differential interference contrast optics (Zeiss-Nomarski). The degree of antibody staining was evaluated as O (no reactivity), + (few positive cells), + + (at least one third of the cells positive), + + + (most cells positive), + + + + (close to all cells strongly positive). Since differences between + and O staining were less clear cut than between + + and + staining, it was decided to count as "positive" a staining graded as + + or greater. Both neoplastic and stroma cells were observed in tumor samples; the staining recorded referred to that of the tumor cells, since the stroma cells were not stained at all, or were stained more weakly than the tumor cells.

Determination of Antigen Location

The subcellular localization of antigens was determined by measuring antibody binding to cells before or after permeabilization with non-ionic detergent. Antibodies binding to the cell surface of intact cultured cells were identified by either direct binding assays with $^{125}I$-labelled antibody (Brown et al., *Proc. Natl. Acad. Sci. U.S.A.* (1981) 78:539–543) or by indirect fluorescence using the (FACS) II cell sorter. Antibodies binding to intracellular locations were determined by direct binding of $^{125}I$-labelled antibody to cells following fixation with paraformaldehyde and subsequent permeabilization with the non-ionic detergent NP-40.

Binding Assays (a) For binding assays performed by using radiolabelled antibodies (Brown et al., supra), cultured cells ($10^6$) were incubated at 4° C. for 30 min with $10^6$ cpm of $^{125}$I-labelled antibody in 100 μl of heat-activated (30 min at 56° C.) fetal calf serum in culture medium. After the addition of 5 ml of PBS, the cells were pelleted by centrifugation for 10 min at 250 X g. The supernatant was aspirated, and the pellet was counted for $^{125}$I. To measure nonspecific binding, parallel incubations were performed with 10 μg of unlabelled antibody as a competitor (Brown, et al., supra). In some instances binding assays were carried out in an analogous fashion on cells monolayers attached to plastic culture dishes.

(b) For binding assays performed on the FACS II cell sorter, cells were removed from their substrata using PBS containing 5 mM ethylenediamine tetraacetic acid (EDTA). Samples containing $1 \times 10^5$ cells were incubated first with monoclonal antibody at a concentration of 2 μg/ml followed by fluorescein-conjugated goat anti-mouse antibody at a 1:200 dilution. Cells were then washed and resuspended in culture medium. Immediately prior to FACS analysis, propidium iodide was added to a final concentration of 1 μg/ml to stain non-viable cells. During FACS analysis, cells emitting red fluorescence were electronically gated out so that only viable cells were examined. The mean intensity of fluorescein fluorescence was then determined for each antibody. Negative controls consisted of samples in which monoclonal antibody was omitted; positive controls consisted of monoclonal antibodies to HLA type 1 histocompatibility antigens. Staining was regarded as positive if the mean channel fluorescein was at least 3 times background.

Protein Antigen Determination

In order to identify protein antigens, lung carcinoma cells were surface radioionated or metabolically labelled with $^{35}$S-methionine. Antigens were isolated from cell lysates by incubation with monoclonal antibody, addition of goat anti-mouse IgG, and adsorption to *S. aureus*. Immune precipitates were washed and analyzed by sodium dodecylsulfate-polyacrylamide gel electrophoresis (SDS-PAGE) (10–20% acrylamide) as described (Brown et al., supra).

Determination of Reactivity of Antibodies to Glycolipids

Antibodies were tested for reactivity to glycolipid antigens by incubation with purified glycolipids adsorbed to microtest wells (along with cholesterol and lecithin) and with thin layer chromatography plates on which glycolipids had been fractionated. Bound antibody was detected by incubation with antiserum to mouse immunoglobulin and radioiodinated protein A.

Isotype Determination (a) Ouchterlony immunodiffusion

An aliquot of supernatant of particular hydridoma cells was placed into the center well of a 2% agar plate. Monospecific rabbit anti-mouse Ig isotypes antibodies (Meloy) were placed in the outer wells and the plate was incubated for 2 hr at room temperature and overnight at 4° C.

(b) Flexible polyvinylchloride 96 well plates (Costar) were coated with 0.1 mg/ml goat anti-mouse Ig antibodies for 2 hr at 37° C. and countercoated with a 3% BSA solution for 2 hr at 37° C. The hydridoma supernatant was then incubated at 37° C. for 2 h. After washing with PBS bovine serum albumin (BSA) plates were incubated at 37° C. for 2 hr with monospecific rabbit anti-mouse Ig isotype antibodies coupled to peroxidase (Zymed). After washing, plates were incubated with 1 mg/ml orthophenylenediamine and 0.03% $H_2O_2$ in 0.1 M citrate buffer pH 4.5. Optical density at 630 nm was determined on a Dynatec ELISA plate reader.

Staphylococcal Protein A Binding Assay

Microtiter wells were incubated with 5% NCS in PBS plus 0.02% $NaN_3$ and the supernatant was aspirated. Twenty-five μl of a suspension of epidermal cells ($2 \times 10^7$ cells/ml) were added to each well and incubated with 25 μl of a particular antibody for 1 hr at room temperature. The plates were centrifuged at 1200 rpm for 7 min, washed twice with 50% NCS/PBS/$NaN_3$ and 25 μl $^{125}$I-staphylococcal protein A (about 50,000 cpm/25 l) were added. The plates were incubated for 1 hr at 25° C., washed twice with 5% NCS/PBS/$NaN_3$ and dried. The bottom of the wells were cut off and counted in a gamma counter.

EXAMPLE

Preparation of Monoclonal Antibodies

Monoclonal antibodies were produced by immunizing 3-month-old BALB/c mice with human tissues of one of four different sources: (1) pleural effusions from patients with metastic non-small cell lung carcinoma, (2) cultured cells from a non-small cell lung carcinoma, and (3) lung tissue from 3–4 months-old human embryos. The immunizations were performed by injecting the mice intraperitoneally 3–4 times with approximately $10^7$ cells. Three days after the last immunization, the spleens were removed, suspended in culture medium and fused with NS1 mouse myeloma cells (Köhler and Milstein, supra). The mixtures were seeded to form low density cultures originating from single fused cells (clones); the techniques used for the hybridization have been previously described by Yeh, et al., *Int. J. Cancer* (1979) 29:269–275.

Supernatants from hybrid cells were screened by using both an ELISA assay and an autoradiographic indirect $^{125}$I-labelled protein A assay (Brown et al.,) *J. Immunol. Meth.* (1979) 31:201–209 against extracts from the tumors used for immunization which contained, i.e., cell membranes. These extracts were prepared using a procedure modified from Colcher et al., *Cancer Res.*, (1981) 42:1451–1459; Yeh et al., supra. For this, tissues were washed with PBS and suspended, which for intact tumors was done by pressing through a stainless steel screen. After this 1 mM $NaHCO_3$ containing 1 mM phenylmethylsulfonylfluoride (Calbiochem-Behring Corp., San Diego, Calif.) was added, and the material was then homogenized on ice, with 50 strokes of the B pestle of a Dounce homogenizer. After centrifugation for 15 min at 27,000 $\times$X g, the supernatant was removed, and the pellet was resuspended in PBS, sonicated for 1 min, and stored at −70° C.

Hybridomas which produced antibodies binding to the cell membrane extracts were cloned, expanded in vitro, and further tested for antibody specificity. This testing was carried out by using the Immunohistological Technique described above, in which the ability of the antibodies to bind to frozen sections of lung carcinomas, other tumors and normal human tissues were tested.

Those hybridomas which produced antibody of apparent specificity for human lung cancer were recloned, expanded and injected into pristane-primed 3-month old BALB/c mice, where they grew as ascites tumors.

Antibodies secreted into the ascites were purified on protein A Sepharose (Ey et al., *Immunochemistry* (1978) 15:429) or by gel filtration in Sephacryl S-300. Purified antibodies were used for further characterization which included additional specificity tests by immunohistology, binding assays on intact cells to determine which antibodies bound to the cell surface, and the radioimmunoprecipitation tests as described above.

Monoclonal antibody L6 was produced from the corresponding hybridoma as described above. This antibody exhibited the properties indicated above in this specification.

The cell line, designated L6 was deposited at the A.T.C.C. on Dec. 6, 1984, and received accession number HB 8677.

EXAMPLE

Reactivity of Certain Glycolipids with L6 Antibody

Studies on the reactivity of the L6 antibody were conducted according to standard procedures such as described by Kannagi et al. (1983) *Cancer Research* 43:4997–5005 and Nudelman et al. (1982) *J. Biol. Chem.* 257:12752–12756. Defined glycolipids were assayed for reactivity with the L6 antibody. Glycolipids separated on TLC were immunostrained by the antibody and solid-phase radioimmunoassays were carried out on glycolipids which had been coated onto plastic wells. The data are summarized in Table I.

TABLE I

| Structure | Reactivity with L6 |
|---|---|
| Asialo GalNAc—GM$_1$ | |
| GalNAcβ1→4Galβ1→GalNAcβ1→4Galβ1→4Glcβ1→1Cer | +++ |
| CROSS-REACTIONS | |
| Gg$_3$ (asialo GM$_2$) | |
| GalNAcβ1→4Galβ1→4Glcβ1→1Cer | ++ |
| Gg$_4$ (asialo GM$_1$) | |
| Galβ1→3GalNAcβ1→4Galβ1→4Glcβ1→1Cer | + |
| x$_2$ glycolipid | |
| GalNAcβ1→3Galβ1→4GlcNAcβ1→3Galβ1→4Glcβ1→1Cer | ± |
| Gb$_3$ (CTH; p$^k$ antigen) | |
| Galα1→4Galβ1→4Glcβ1→1Cer | − |
| Globoside (P antigen) | |
| GalNacβ1→3Galα1→4Galβ1→4Glcβ1→1Cer | − |
| Paragloboside | |
| Galβ1→4GlcNAcβ1→3Galβ1→4Glcβ1→1Cer | − |
| 5 other glycolipid structures | − |

The L6 antibody reacted specifically with asialo GalNAc-GM$_2$ and asialo GM$_2$ with the strongest reaction observed with asialo GalNAc-GM$_1$. A weak reactivity was found with gangliotetraosylceramide (asialo GM$_1$) and x$_2$ glycolipid (structure defined in Table I). Globoside, globotriaosylceramide, lactosylceramide, paragloboside (lactotetraosylceramide), glycolipids with Le$^x$ and Le$^y$ structures, and gangliosides with ganglio- and lacto-series structures were all negative. It appears, therefore, that the L6 antibody recognizes the following sequence.

GalNAcβ1→4Galβ1→3GalNAcβ1→4Galβ1→R wherein R is an undefined carbohydrate.

EXAMPLE

Antibody-Dependent Cellular Cytotoxicity (ADCC)

This study was carried out by a method previously described by Hellstrom et al., *PNAS* 82: 1499, 1985, by incubating mixtures of $^{51}$Cr-labelled target cells (2981 lung carcinoma), antibodies (various dilutions) and lymphocytes (various ratios between lymphotcytes and target cells) for 4 hours and measuring the amounts of $^{51}$Cr released into the supernatant. The experiment and results are summarized in Table 2.

TABLE 2

| L6 Antibody (μg/ml) | (% Cytotoxicity of ADCC) |
|---|---|
| 10 μg/ml, Batch 1 | 84 |
| 10 μg/ml, Batch 2 | 76 |
| 10 μg/ml, Batch 3 | 83 |
| 10 μg/ml, Batch 4 | 66 |
| 10 μg/ml, Batch 5 | 74 |
| 0 μg/ml | 18 |
| (no human lymphocytes, Batch 1) | 0 |

Therefore, antibody L6 mediated ADCC when tested on target cells expressing the L6 antigen.

EXAMPLE

Antibody-Mediated Cytotoxicity in the Presence of Human Complement

To test whether antibody L6 can destroy tumor cells in the presence of human complement, $^{51}$Cr-labelled target cells (2981 lung carcinoma) were incubated for 4 hours with antibody and human complement, following established procedures (Hellstrom et al, *PNAS* 82: 1499, 1985). The experiment and results are summarized in Table 3.

TABLE 3

| L6 Antibody (μg/ml) | Cytotoxicity |
|---|---|
| 50 | 3 |
| 10 | 54 |
| 1 | 43 |
| 50 (no complement) | 1 |
| 10 (no complement) | 3 |
| target cells plus medium | 0 |

Antibodies activating human complement are of interest for at least two reasons: they may directly kill tumor cells and they may be able to induce an inflammatory response in the tumor area with activated macrophages and other cells which are preferentially cytolytic to neoplastic as compared to normal cells.

EXAMPLE

Specificity Testing with Immunohistology Against Various Tumors

| Specificity Testing with Immunohistology Against Various Tumors | |
|---|---|
| Tissue | Antibody L6 |
| Lung Carcinoma | |
| Adeno | 18/19 |
| Squamous | 8/10 |
| Small Cell | 2/6 |
| Large Cell | 2/2 |
| Breast Carcinoma | 13/16 |
| Colon Carcinoma | 9/9 |
| Melanoma | 1 |

| Specificity Testing with Immunohistology Against Various Tumors | |
| --- | --- |
| Tissue | Antibody L6 |
| "Other Tumors" (Sarcoma, etc) | 1/9 |

The invention has been described in detail with particular reference to the above embodiments. It will be understood, however, that variations and modifications can be effected within the spirit and scope of the invention.

What is claimed is:

1. A method for determining the presence of a malignant condition in a tissue specimen obtained from an individual, comprising:
   (a) contacting the tissue specimen with a monoclonal antibody, the antigen combining site of which competitively inhibits the immunospecific binding of monoclonal antibody L6, produced by hybridoma HB8677 as deposited with the ATCC, to its target antigen; and
   (b) detecting whether the monoclonal antibody immunospecifically binds to the tissue specimen, in which immunospecific binding of the monoclonal antibody to the tissue specimen indicates the presence of a malignant condition in the tissue specimen.

2. The method according to claim 1 in which the binding of the monoclonal antibody to the tissue specimen is detected in step (b) by contacting the tissue specimen with a conjugate of a label and a specific binding partner for the monoclonal antibody, the label being capable of producing a detectable signal, so that detection of the signal bound to the tissue specimen indicates the binding of the monoclonal antibody to the tissue specimen.

3. The method according to claim 2 in which the binding partner comprises an antibody specific for the monoclonal antibody.

4. The method according to claim 2 or 3 in which the label comprises a fluorescer, a radiolabel, a chromophore or an enzyme.

5. The method according to claim 1 in which the monoclonal antibody is conjugated to a label capable of producing a detectable signal so that detection of the signal bound to the tissue specimen indicates the binding of the monoclonal antibody conjugate to the tissue specimen.

6. The method according to claim 5 in which the label comprises a fluorescer, a radiolabel, a chromophore or an enzyme.

7. The method according to claim 1 in which the tissue specimen comprises a lung, colon or breast tissue specimen.

8. A method for determining the presence of a maligant condition in a tissue specimen obtained from an individual comprising:
   (a) contacting the tissue specimen with an Fab, F(ab')$_2$ or Fv fragment of a monoclonal antibody, the antigen combining site of which competitively inhibits the immunospecific binding of monoclonal antibody L6, produced by hybridoma HB8677 as deposited with the ATCC, to its target antigen; and
   (b) detecting whether the Fab, F(ab')$_2$ or Fv fragment immunospecifically binds to the tissue specimen, in which immunospecific binding of the Fab, F(ab')$_2$ or Fv fragment to the tissue specimen indicates the presence of a malignant condition.

9. The method according to claim 8 in which the binding of the Fab, F(ab')$_2$ or Fv fragment to the tissue specimen is detected in step (b) by contacting the tissue specimen with a conjugate of a label and a specific binding partner for the Fab, F(ab')$_2$ or Fv fragment, the label being capable of producing a detectable signal, so that detection of the signal bound to the tissue specimen indicates the binding of the Fab, F(ab')$_2$ or Fv fragment.

10. The method according to claim 9 in which the binding partner comprises an antibody specific for the Fab, F(ab')$_2$ or Fv fragment.

11. The method according to claim 9 or 10 in which the label comprises a fluorescer, a radiolabel, a chromophore or an enzyme.

12. The method according to claim 8 in which the Fab, F(ab')$_2$ or Fv fragment is conjugated to a label capable of producing a detectable signal so that detection of the signal bound to the tissue specimen indicates the binding of the Fab, F(ab')$_2$ or Fv conjugate to the tissue specimen.

13. The method according to claim 12 in which the label comprises a fluorescer, a radiolabel, a chromophore, or an enzyme.

14. The method according to claim 8 in which the tissue specimen comprises a lung, colon, or breast tissue specimen.

15. A method for determining the presence of a malignant condition in a tissue specimen obtained from an individual comprising:
   (a) contacting the tissue specimen with monoclonal antibody L6 which is produced by a hybridoma cell line having the identifying characteristics of HB8677, as deposited with the ATCC; and
   (b) detecting whether the monoclonal antibody L6 immunospecifically binds to the tissue specimen, in which binding of the monoclonal antibody L6 to the tissue specimen indicates the presence of a malignant condition in the tissue specimen.

16. The method according to claim 15 in which the binding of monoclonal antibody L6 to the tissue specimen is detected in step (b) by contacting the tissue specimen with a conjugate of a label and a specific binding partner for the monoclonal antibody L6, the label being capable of producing a detectable signal, so that detection of the signal bound to the tissue specimen indicates the binding of the monoclonal antibody L6 to the tissue specimen.

17. The method according to claim 16 in which the binding partner comprises an antibody specific for the monoclonal antibody L6.

18. The method according to claim 16 or 17 in which the label comprises a fluorescer, a radiolabel, a chromophore or an enzyme.

19. The method according to claim 15 in which the monoclonal antibody L6 is conjugated to a label capable of producing a detectable signal so that detection of the signal bound to the tissue specimen indicates the binding of the monoclonal antibody L6 conjugate to the tissue specimen.

20. The method according to claim 19 in which the label comprises a fluorescer, a radiolabel, a chromophore or an enzyme.

21. The method according to claim 15 in which the tissue specimen comprises a lung, colon or breast tissue specimen.

22. A method for determining the presence of a malignant condition in a tissue specimen obtained from an individual, comprising:
  (a) contacting the tissue specimen with an Fab, F(ab')$_2$ or Fv fragment of monoclonal antibody L6 which is produced by a hybridoma cell line having the identifying characteristics of HB8677, as deposited with the ATCC; and
  (b) detecting whether the Fab, F(ab')$_2$ or Fv fragment immunospecifically binds to the tissue specimen, in which immunospecific binding of the Fab, F(ab')$_2$ or Fv fragment to the tissue specimen indicates the presence of a malignant condition.

23. The method according to claim 22 in which the binding of the Fab, F(ab')$_2$ or Fv fragment to the tissue specimen is detected in step (b) by contacting the tissue specimen with a conjugate of a label and a specific binding partner for the Fab, F(ab')$_2$ or Fv fragment, the label being capable of producing a detectable signal so that detection of the signal bound to the tissue specimen indicates the binding of the Fab, F(ab')$_2$ or Fv fragment to the tissue specimen.

24. The method according to claim 22 in which the binding partner comprises an antibody specific for the Fab, F(ab')$_2$ or Fv fragment.

25. The method according to claim 23 or 24 in which the label comprises a fluorescer, a radiolabel, a chromophore or an enzyme.

26. The method according to claim 22 in which the Fab, F(ab')$_2$ or Fv fragment is conjugated to a label capable of producing a detectable signal so that the detection of the signal bound to the tissue specimen indicates the binding of the Fab, F(ab')$_2$ or Fv conjugate to the tissue specimen.

27. The method according to claim 26 in which the label comprises a fluorescer, a radiolabel, a chromophore, or an enzyme.

28. The method according to claim 22 in which the tissue specimen comprises a lung, colon, or breast tissue specimen.

* * * * *

UNITED STATES PATENT AND TRADEMARK OFFICE
CERTIFICATE OF CORRECTION

PATENT NO.  : 4,906,562

DATED       : March 6, 1990

INVENTOR(S) : Ingegerd Hellstrom; Joseph P. Brown; Karl E. Hellstrom;
              Diane Horn; Peter Linsley It is certified that error appears in the above-identified patent and that said Letters Patent is hereby corrected as shown below:

In the first column of the cover page of U.S. Patent 4,906,502, at Item [63] under "Related U.S. Application Data" the text which reads: "Continuation-in-part of Ser. No. 684,759, Dec. 21, 1984, abandoned." should be amended to read as follows:

-- Continuation-in-part of Ser. No. 684,759, Dec. 21, 1984, which issued to U.S. Patent No. 4,935,495 on June 19, 1990.--.

Signed and Sealed this

Fifth Day of January, 1993

Attest:

DOUGLAS B. COMER

*Attesting Officer*      *Acting Commissioner of Patents and Trademarks*